United States Patent [19]

Welch et al.

[11] Patent Number: 5,010,088
[45] Date of Patent: Apr. 23, 1991

[54] 6-(4-HYDROXYPIPERIDINO) CARBOSLYRIL

[75] Inventors: Richard M. Welch, Raleigh; Alan R. Brown, Durham; Arthur P. Phillips, Raleigh, all of N.C.

[73] Assignee: Burroughs Wellcome Co., Research Triangle Park, N.C.

[21] Appl. No.: 398,219

[22] Filed: Aug. 24, 1989

[30] Foreign Application Priority Data

Aug. 25, 1988 [GB] United Kingdom ............... 8820174

[51] Int. Cl.⁵ .................. C07D 401/04; A61K 31/47
[52] U.S. Cl. ..................................... 514/312; 546/157
[58] Field of Search ..................... 546/157; 514/312

[56] References Cited

U.S. PATENT DOCUMENTS

| 4,593,035 | 6/1986 | Tominaga | 514/312 |
| 4,886,809 | 12/1989 | Tamada | 514/312 |
| 4,921,862 | 5/1990 | Walker | 546/157 |
| 4,937,248 | 6/1990 | Phillips | 514/312 |

FOREIGN PATENT DOCUMENTS 0236140 9/1987 European Pat. Off. .
0356230 A1 2/1990 European Pat. Off. .
1145162 7/1985 Japan ................................. 514/312

OTHER PUBLICATIONS

Chem. Abstracts, vol. 107, Entry 77827k (1987), abstracts JP 62 48 679 (Otsuka).

Primary Examiner—Donald G. Daus
Attorney, Agent, or Firm—Donald Brown; Hannah O. Green; Lawrence A. Nielsen

[57] ABSTRACT

The present invention is concerned with the compound of formula (I)

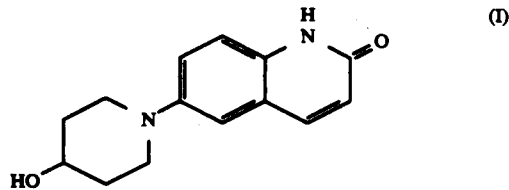

and esters and acid addition salts thereof having positive inotrope effect.

11 Claims, No Drawings

6-(4-HYDROXYPIPERIDINO) CARBOSLYRIL

The present invention relates to a novel quinoline derivative and its use in medicine as an inotropic agent suitable for use in the treatment of congestive heart failure.

Congestive heart failure is defined as the condition whereby the heart is incapable of supplying an adequate volume of blood to organs commensurate with their needs. This disorder can be caused by a primary deficiency in cardiac muscle (deteriorating myocardial contractility) or secondary to hypertension or various cardiomyopathies. The depressed contractile function leads to a reduced ejection fraction (incomplete emptying of the ventricles after systole) with resulting increased myocardial wall stretch and further reduction in contractility. A useful cardiotonic drug should have positive inotropic property (the ability to increase the force and rate of myocardial contractions) to improve ejection fraction and also vasodilatory properties to further facilitate cardiac emptying.

European Patent Application No. 87311275.9 describes 6-piperidinocarbostyril and its acid addition salts and their use as inotropic/vasodilatory agents. We have now identified a metabolite of 6-piperidinocarbostyril, viz 6-(4-hydroxypiperidino)carbostyril, which, together with its physiologically functional esters and acid addition salts, possesses similar inotropic activity to 6-piperidinocarbostyril, but has a reduced vasodilatory effect which renders it particularly suitable for the treatment of certain categories of heart failure patient for which 6-piperidinocarbostyril is less desirable or must be used in conjunction with another drug.

According to the present invention, therefore, there is provided a novel compound of formula (I)

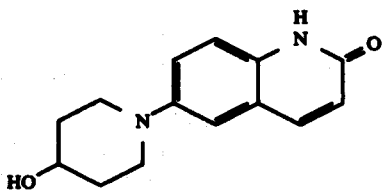

6-(4-hydroxypiperidino)carbostyril, also known as 6-(4-hydroxypiperidino)-2(1H)-quinolinone, hereinafter referred to as "compound (I)", and its physiologically functional esters and acid addition salts. Compounds according to the invention have been found to possess a positive inotropic effect which renders them useful for the treatment of, for example, congestive heart failure or heat failure associated with cardiomyopathy, myocardial infarction, or cardiogenic shock, while avoiding or obviating problems associated with the use of cardiac glycosides and sympathomimetics. The compounds of the invention have been found to have a reduced vasodilatory effect which is of benefit in the treatment of certain categories of heart failure patient, for example, those having low blood pressure.

As indicated, the present invention includes physiologically functional esters and acid addition salts of compound (I). Such esters include, for example, alkyl esters such as the acetate, aryl esters such as the benzoate and esters derived from aminoacids. The acid addition salts are formed by protonation of the basic nitrogen. While it will be appreciated that acid addition salts of compound (I) may be formed with a large number of organic and inorganic acids, for therapeutic use only pharmaceutically acceptable acid addition salts are appropriate. Such pharmaceutically acceptable salts include, but are not limited to, those derived from hydrochloric, hydrobromic, phosphoric, malic, maleic, fumaric, citric, sulphuric, lactic, and tartaric acid. The hydrochloride salt is particularly preferred. The present invention also includes non-pharmaceutically acceptable acid addition salts which may be used for isolating, purifying, or characterizing compound (I).

The present invention also includes:

(a) a method for the treatment of clinical conditions wherein a positive inotropic agent is indicated in a mammal in need thereof which comprises administering to the mammal, for example, a human, an effective treatment amount of compound (I) or of a physiologically functional ester or acid addition salt thereof;

(b) compound (I) or a physiologically functional ester or acid addition salt thereof for use in human medical therapy, for example, the treatment of clinical conditions wherein a positive inotropic agent is indicated;

(c) the use of compound (I) or a physiologically functional ester or acid addition salt thereof in the manufacture of a pharmaceutical formulation for the treatment of clinical conditions wherein a positive inotropic agent is indicated.

The amount of the active compound, i.e. compound (I) or a physiologically functional ester or acid addition salt thereof, required to produce the desired level of inotropic effects in mammals, including humans, will, of course, vary with the mode of administration and the condition of the mammal undergoing treatment and is ultimately at the discretion of the physician or veterinarian. However, a suitable oral dose of compound (I) for a mammal, for example, a human, is in the range 0.01 to 100 mg per kilogram of body weight per day, preferably in the range 0.05 to 20 mg/kg body weight per day and most preferably in the range 0.5 to 20 mg/kg body weight per day. The desired dose is preferably presented as two to four sub-doses administered at appropriate intervals throughout the day. Thus, where four sub-doses are employed, each will preferably lie in the range 0.0125 to 5.0 mg/kg. The corresponding doses of physiologically functional esters and acid addition salts of compound (I) are adjusted accordingly to provide the appropriate amounts of compound (I).

Compound (I) or a physiologically functional ester or acid addition salt thereof (hereinafter collectively referred to as the active compound) can be given as an intravenous sterile bolus injection from once to about four times per day. A suitable dose for a mammal is in the range 0.001 to 10.0 mg/kg body weight, preferably in the range 0.01 to 0.25 mg/kg body weight per injection. The active compound can also be administered as an intravenous infusion at doses that maintain the desired increase of cardiac performance.

While it is possible for the active compound to be administered alone as the raw chemical, it is preferable to present it in a pharmaceutical formulation. Formulations of the present invention, both veterinary and for human medical use, comprise the active compound together with one or more pharmaceutically acceptable carrier(s) thereof and, optionally, other therapeutic ingredients. The carrier(s) must be pharmaceutically acceptable in the sense of being compatible with the other ingredients of the formulation and not deleterious to the recipient thereof. The other therapeutic ingredient(s) may include other inotropic agents or vasodilating agents. Accessory ingredients such as preservative, colouring, sweetening, flavouring, etc. agents may also be added to enhance the appearance, taste, or storage life of the formulation.

The formulations include those suitable for oral, rectal, topical, buccal (sub-lingual), parenteral (including subcutaneous, intramuscular, intradermal and intravenous), or transdermal administration. They may conveniently be presented in unit dosage form and may be prepared by any of the methods well known in the art of pharmacy. All methods include the step of bringing the active compound into association with the carrier(s) and any accessory ingredient(s). In general, the formulations are prepared by uniformly and intimately bringing the active compound into association with a liquid carrier or a finely divided solid carrier, or both, and then, if necessary, shaping the product into the desired formulation.

Formulations of the present invention suitable for oral administration may be presented as discrete units such as capsules, cachets, tablets, or lozenges, each containing a predetermined amount of the active compound; as a powder or granules; or as a suspension in an aqueous liquid or non-aqueous liquid such as a syrup, an elixir, an emulsion, or a draught. The active compound may also be presented as a bolus, electuary, or paste. Tablets or capsules may be prepared as sustained release formulations.

A tablet may be made by compression or moulding, optionally with one or more accessory ingredients. Compressed tablets may be prepared by compressing in a suitable machine a free-flowing form (such as a powder or granules) of the active compound optionally mixed with a binder, lubricant, dispersing agent, or other agent(s) to enhance appearance or promote stability. Moulded tablets may be made by moulding in a suitable machine from a mixture of ingredients similar to those used in producing compressed tablets.

A syrup may be made by adding the active compound to a concentrated, aqueous solution of sugar, for example, sucrose, to which may also be added any accessory ingredient(s). Such accessory ingredient(s) may include flavourings, agent(s) to retard crystallization and agent(s) to increase the solubility of the other ingredients.

Formulations suitable for rectal administration are preferably presented as unit dose suppositories. These may be prepared by admixing a compound of formula (I), or a physiologically functional ester or acid addition salt thereof, with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include vaseline, lanoline, polyethylene glycols, alcohols and combinations of two or more thereof. The active compound is generally present at a concentration of from 0.1 to 15% w/w, for example, from 0.5 to 2% w/w.

Formulations suitable for buccal (sub-lingual) administration include lozenges comprising a compound of formula (I), or a physiologically functional ester or acid addition salt thereof, in a flavoured base, usually sucrose and acacia or tragacanth, and pastilles comprising the active compound in an inert base such as gelatin and glycerin or sucrose and acacia.

Formulations suitable for parenteral administration conveniently comprise a sterile aqueous preparation of the active compound which is preferably isotonic with the blood of the recipient. These preparations are preferably administered intravenously, although administration may also be effected by means of subcutaneous, intramuscular, or intradermal injection. Such preparations may conveniently be prepared by admixing the compound with water or a glycine buffer and rendering the resulting solution sterile and isotonic with the blood. Injectable formulations according to the invention will generally contain from 0.1 to 5% w/v of the active compound and be administered at a rate of 0.1 ml/min/kg.

Formulations for transdermal administration may be delivered by iontophoresis (see, for example, Pharmaceutical Research 3(6), 318, (1986)) and typically take the form of an optionally buffered aqueous solution of a compound of formula (I) or of a physiologically functional ester or acid addition salt thereof. Suitable formulations comprise citrate or bis/tris buffer (pH 6) or ethanol/water containing from 0.1 to 0.2M active compound.

The present invention further includes a process for the preparation of compound (I) and physiologically functional esters and acid addition salts thereof which comprises reacting 6-aminocarbostyril with a compound of formula L—$(CH_2)_2CH(OH)(CH_2)_2$—L', wherein L and L', which may be the same or different, are suitable leaving groups, such as bromo, in the presence of a base, such as anhydrous sodium carbonate, and optionally converting the resulting compound (I) into a physiologically functional ester or acid addition salt thereof. The reaction of the 6-aminocarbostyril and the substituted pentan-3-ol is typically carried out in an aprotic solvent, such as dimethylformamide, at a temperature of about 100° C. The compound (I) may be converted into an ester thereof in conventional manner, for example, by treatment with the appropriate halide in the presence of base, or into an acid addition salt by treatment with the appropriate acid using, for example, an alcoholic solution thereof.

The following examples are provided to illustrate the present invention and are in no way to be construed as a limitation thereof.

EXAMPLE 1

6-(4-Hydroxypiperidino)carbostyril a. 6-Nitrocarbostyril

Nitric acid (70%), 2.3 mL, was added dropwise to a stirred mixture of 2-hydroxyquinoline (available commercially or by one of the methods described in Beilstein 21, 77), 3.5 g (0.024 mole), in 20 mL of concentrated sulfuric acid at 0° C. The reaction mixture was stirred for 2 hours at room temperature and then poured into ice and water. The resulting solid was collected by filtration, washed with cold water and then digested twice with hot methanol to yield 3 g (67%) of 6-nitrocarbostyril as crystals; m.p. 280°–282° C.

Anal. calcd. for $C_9H_6N_2O_3$: C, 56.84; H, 3.18; N, 14.74. Found: C, 56.81; H, 3.18; N, 14.72.

b. 6-Aminocarbostyril

In a Parr catalytic hydrogenation apparatus 6-nitrocarbostyril, 5.3 g (0.028 mole), in 150 mL of methanol and 0.5 g PtO₂ were shaken in a hydrogen atmosphere. The resulting yellow solid was extracted with refluxing methanol and the extract evaporated to yield 6-aminocarbostyril, 3.5 g, as yellow crystals; m.p. 315°-317° C.

Anal. calcd. for $C_9H_8N_2O$: C, 67.48; H, 5.03; N, 17.49. Found: C, 67.28; H, 4.98; N, 17.38.

c. 3-Hydroxy-1,5-dibromopentane

4-Hydroxytetrahydropyran (Chem. Ber. 88, 1053 (1955)), 20 g (0.2 mole), was saturated with HBr for an hour at 100°-120° C. The mixture was then cooled, taken up in methylene chloride and washed with ice-cold aqueous NaOH and water. The organic phase was dried over anhydrous potassium carbonate, evaporated and the residue distilled to give 35.5 g of oil having a bp at 13 mm Hg of 136°-140° C. Elemental analysis was consistent with the oil comprising a mixture of 1,3,5-tribromopentane and the desired product, 3-hydroxy-1,5-dibromopentane. The oil was used in step d without purification.

d. 6-(4-Hydroxypiperidino)carbostyril

A mixture of 6-aminocarbostyril, 1.6 g (0.01 mole), crude bromopentanes from step c, 3.1 g, anhydrous sodium carbonate, 2.0 g (0.020 mole), and dimethylformamide, 15 mL, was heated for 4.5 hours at 100° C. with occasional stirring. The mixture was then cooled and diluted with water, 150 mL, to give a pasty precipitate which was filtered off and washed with water to give a sticky solid (2.9 g). The solid was taken up in hot methanol and the insoluble material filtered off (0.6 g, mp 270°-280° C.). Further treatment with hot methanol gave 0.4 g of the desired product, mp 280°-283° C.

Anal. calcd. for $C_{14}H_{16}N_2O_2$: C, 68.83; H, 6.60; N, 11.44. Found: C, 68,76; H, 6.64; N, 11.40.

EXAMPLE 2

6-(4-Hydroxypiperidino)carbostyril hydrochloride 6-(4-Hydroxypiperidino)carbostyril, 0.1 g (0.002 mole), was suspended in 15 mL methanol. Five mL ethanolic hydrogen chloride was added and the mixture digested on a steam bath for 15 minutes until part of the methanol had evaporated. After cooling, filtration and washing with ethyl acetate, the resulting white crystals, 0.05 g, were recrystallized by dissolving in warm methanol and adding ethyl acetate. The yield was 0.05 g 6-(4-hydroxypiperidino)carbostyril hydrochloride; m.p. 259°-262° C.

Anal. calcd. for $C_{14}H_{16}N_2O_2$: C, 57.14; H, 6.34; N, 9.52; Cl, 12.05. Found: C, 56.92; H, 6.32; N, 9.46; Cl, 11.98.

EXAMPLE 3

6-(4-Acetoxypiperidino)-2(1H)-quinolinone

A mixture of 6-(4-hydroxypiperidino)carbostyril (0.25 g), acetic anhydride (0.4 g) and dry pyridine (4 mL) was heated at 100° C. for 3 hours. The reaction mixture was cooled and water (about 35 mL) and sodium bicarbonate (0.6 g) were added. The mixture was chilled in ice and stirred. The resulting white solid was removed by filtration, washed with water and dried to give 6-(4-acetoxypiperidino)-2(1H)-quinolinone. ¼ hydrate (0.3 g); m.p. 245°-250° C.

Anal. calcd. for $C_{16}H_{18}N_2O_3 \cdot \frac{1}{4}H_2O$: C, 66.08; H, 6.41; N, 9.63. Found: C, 66.07; H, 6.29; N, 9.47.

Recrystallization from ethyl acetate gave 6-(4-acetoxypiperidino)-2(1H)-quinolinone, m.p. 250°-252° C.

Anal. calcd. for $C_{16}H_{18}N_2O_3$: C, 67.12; H, 6.34; N, 9.78. Found: C, 66.98; H, 6.40; N, 9.76.

EXAMPLE 4

6-(4-Benzoyloxypiperidino)-2(1H)-quinolinone

A mixture of 6-(4-hydroxypiperidino)carbostyril (0.25 g), benzoyl chloride (0.17 g) and dry pyridine (2 mL) was heated for 3 hours at 100° C. The reaction mixture was cooled and water (about 25 mL) and sodium bicarbonate (1 g) were added. The mixture was chilled in ice and stirred. The resulting solid was removed by filtration, washed with water and dried to give crude 6-(4-benzoyloxypiperidino)-2(1H)-quinolinone (0.25 g). Recrystallization twice from ethyl acetate gave 6-(4-benzoyloxypiperidino)-2(1H)-quinolinone (0.18 g); m.p. 212°-215° C.

Anal. calcd. for $C_{21}H_{20}N_2O_3$: C, 72.40; H, 5.79; N, 7.49. Found: C, 72.31; H, 5.79; N, 8.01.

EXAMPLE 5

In Vitro Inotropic Activity

Cats of either sex (2.5-3.5 kg) were anaesthetized with sodium pentobarbital (30 mg/kg, i.p.). Each cat's chest was opened and the heart excised. Papillary muscles were dissected from the ventricular cavity and placed against a punctate electrode in a tissue bath containing 20 mL of Krebs-Henseleit buffer. The buffer was gassed with a mixture of 95% $O_2$ and 5% $CO_2$ and maintained at a temperature of 34° C. The tissues were put under a resting tension of 1.0 g and stimulated through the punctate electrode at a voltage 30% above threshold with square waves of 5 msec duration and a frequency of 5 Hz.

The force generated by the tissues was measured using isometric force transducers and recorded continuously on a polygraph. The test compound, in aqueous solution, was added to the organ bath at increasing concentrations in cumulative fashion in half log increments to give a range of bath concentrations of from 1 to 300 μM. After each addition, the effect was observed for at least two minutes. If an effect was detected, the tissue was allowed to attain steady state before the subsequent dose was added to the tissue bath. A plot of concentration vs the change from control of the force generated by the tissues showed a concentration-dependent increase in force development.

EXAMPLE 6

In Vivo Inotropic and Vasodilatory Activities

Adult male beagle dogs were anaesthetized with sodium pentobarbital by means of a cephalic vein injection (30 mg/kg). The trachea was intubated and the animal mechanically ventilated with room air. Body temperature was maintained by a heating pad placed under the animal. The left and right femoral veins were cannulated for the respective purposes of injecting test agents and continuously infusing anaesthetic (7.0-7.5 mg/kg/hr, sodium pentobarbital). Left ventricular contractility (dP/dt) was measured by a Millar Mikro-Tip catheter pressure transducer positioned in the left intraventricular cavity via the left carotid artery. Arterial blood pressure was measured by a Millar Mikro-Tip catheter pressure transducer positioned in the thoracic aorta via the left femoral artery. Cardiac output was measured by a thermodilution catheter positioned in the pulmonary artery via the right jugular vein using a Spectromed haemodynamic profile computer. Total peripheral resistance (TPR), as a measure of the vascular activity of each test agent, was calculated by dividing the mean arterial blood pressure by cardiac output. Following surgical preparation and a thirty-minute period to allow for stabilization of the baseline haemodynamic parameters, cardiac output was measured in triplicate together with control dP/dt and blood pressure.

The test compound, in aqueous solution, was administered intravenously at a rate of 0.1 ml/kg over a period of one minute in an ascending dose manner at half log increments over a dose range of from 0.03 to 1.0 mg/kg. Doses were administered at 15-minute intervals or until a steady-state pharmacodynamic effect was achieved. Haemodynamic measurements were made at peak effect. A plot of concentration vs dP/dt showed a concentration-dependent increase in left ventricular contractility; a plot of concentration vs TPR showed a concentration-dependent decrease in total peripheral resistance.

Thus the compounds of the invention show positive inotropic and vasodilator activities which render them useful for the treatment of congestive heart failure or heart failure associated with cardiomyopathy, myocardial infarction, ischaemic heart disease, idiopathic cardiac dysfunction, or cardiogenic shock.

EXAMPLE 7

Pharmaceutical Formulations

| a. Tablets | |
|---|---|
| Compound (I) | 50 mg |
| Starch | 132 mg |
| Magnesium stearate | 18 mg |
| Lactose | 45 mg |
| TOTAL: | 245 mg |

Tablets each having the above composition are prepared in a conventional manner.

| b. Ampoules | |
|---|---|
| Compound (I) hydrochloride | 500 mg |
| Sodium chloride | 0.9 mg |
| Distilled water for injection | q.s. to 100 ml |

The above sodium chloride is dissolved in distilled water with warming while stirring. The resulting solution is cooled to 40° C. and the compound of the invention is dissolved therein. Then distilled water for injection is added to the final volume. The mixture is filtered using a suitable filter paper to sterilize and then filled in a ampoule of 1 mL, thus forming the preparation for injection.

We claim:

1. The compound of formula (I)

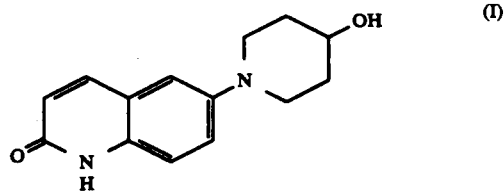

or an acid addition salt or physiologically acceptable ester thereof.

2. The hydrochloride salt of the compound of formula (I) claimed in claim 1.

3. A method of treatment of a disease or disease symptom in a mammal in which a positive inotrope is indicated which comprises administering to said mammal a therapeutically effective amount of the compound of formula (I) as claimed in claim 1 or a physiologically acceptable ester or acid addition salt thereof.

4. A method as claimed in claim 3, wherein the disease or disease symptom is associated with a clinical condition for which a positive inotrope is indicated.

5. A method as claimed in claim 3 wherein the disease or disease symptom is congestive heart failure or heart failure associated with cardiomyopathy, myocardial infarction, or cardiogenic shock.

6. A pharmaceutical formulation comprising the compound of formula (I) as claimed in claim 1, or a physiologically acceptable ester or acid addition salt thereof, one or more pharmaceutically acceptable carriers and/or excipients therefor and, optionally, one or more other therapeutic ingredients.

7. 6-(4-hydroxypiperidino)carbostyril.

8. 6-(4-hydroxypiperidino)carbostyril hydrochloride.

9. 6-(4-Acetoxypiperidino)-2(1H)-quinolinone.

10. 6-(4-Benzoyloxypiperidino)-2(1H)-quinolinone.

11. A pharmaceutically acceptable salt of 6-(4-hydroxypiperidino)carbostyril.

* * * * *

UNITED STATES PATENT AND TRADEMARK OFFICE
CERTIFICATE OF CORRECTION

PATENT NO. : 5,010,088

DATED : April 23, 1991

INVENTOR(S) : Richard M. Welch, Alan R. Brown & Arthur P. Phillips

It is certified that error appears in the above-identified patent and that said Letters Patent is hereby corrected as shown below:

On the title page, item [54] and in column 1, line 2,
"6-(4-HYDROXYPIPERIDINO)CARBOSLYRIL" should read
--6-(4-HYDROXYPIPERIDINO)CARBOSTYRIL--.

Signed and Sealed this

Twenty-fifth Day of August, 1992

Attest:

DOUGLAS B. COMER

Attesting Officer

Acting Commissioner of Patents and Trademarks